United States Patent
Zhou et al.

(10) Patent No.: US 9,820,726 B2
(45) Date of Patent: Nov. 21, 2017

(54) POLYMER MEMBRANE LOCATOR WITH BUILT-IN STRESS RELIEF STRUCTURE

(75) Inventors: Zhengrong Zhou, St. Paul, MN (US); Stephanie M. Board, West St. Paul, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 263 days.

(21) Appl. No.: 12/858,387

(22) Filed: Aug. 17, 2010

(65) Prior Publication Data
US 2011/0046663 A1  Feb. 24, 2011

(51) Int. Cl.
*A61B 17/00* (2006.01)
*A61M 25/10* (2013.01)

(52) U.S. Cl.
CPC ...... *A61B 17/0057* (2013.01); *A61B 2017/00592* (2013.01); *A61B 2017/00654* (2013.01); *A61B 2017/00672* (2013.01); *A61M 25/10* (2013.01); *A61M 25/1002* (2013.01)

(58) Field of Classification Search
CPC .............. A61M 25/10; A61M 25/1002; A61M 25/1011; A61M 2025/1004; A61M 2025/1013; A61M 2025/1081; A61M 2025/1084; A61B 17/12022; A61B 17/12136
USPC .............. 606/191, 198, 200, 213; 604/96.01, 604/101.01, 101.02, 103.05–103.08
See application file for complete search history.

(56) References Cited

U.S. PATENT DOCUMENTS

| | | | | |
|---|---|---|---|---|
| 5,087,246 A | * | 2/1992 | Smith | 604/103.13 |
| 5,250,070 A | * | 10/1993 | Parodi | 606/194 |
| 5,306,250 A | * | 4/1994 | March et al. | 604/104 |
| 5,417,671 A | * | 5/1995 | Jackson | 604/265 |
| 5,458,575 A | * | 10/1995 | Wang | 604/101.02 |
| 5,483,976 A | * | 1/1996 | McLaughlin | A61F 2/0009 128/885 |
| 5,769,871 A | * | 6/1998 | Mers Kelly et al. | 606/200 |
| 5,853,389 A | * | 12/1998 | Hijlkema | 604/103.07 |
| 5,910,102 A | * | 6/1999 | Hastings | 600/3 |
| 6,030,406 A | * | 2/2000 | Davis | A61B 17/00008 604/104 |
| 6,045,569 A | | 4/2000 | Kensey et al. | |
| 6,056,769 A | | 5/2000 | Epstein et al. | |
| 6,090,130 A | | 7/2000 | Nash et al. | |
| 6,179,863 B1 | | 1/2001 | Kensey et al. | |
| 6,214,040 B1 | * | 4/2001 | Jayaraman | 623/1.13 |
| 6,238,412 B1 | * | 5/2001 | Dubrul | A61B 17/22 606/108 |
| 6,464,712 B1 | * | 10/2002 | Epstein | A61B 17/00491 606/213 |
| 6,478,807 B1 | * | 11/2002 | Foreman et al. | 606/194 |
| 6,488,653 B1 | * | 12/2002 | Lombardo | 604/103.06 |
| 6,575,933 B1 | * | 6/2003 | Wittenberger | A61B 18/02 128/898 |

(Continued)

*Primary Examiner* — Dianne Dornbusch
(74) *Attorney, Agent, or Firm* — Holland & Hart

(57) ABSTRACT

A tissue puncture locator device that includes an expandable member, a deformable membrane, and an actuator. The expandable member is movable between an unexpanded position and an expanded position. The deformable membrane extends around at least a portion of the expandable member. The membrane has a stress relief portion. The actuator is operable to move the expandable member between the unexpanded and expanded positions.

19 Claims, 12 Drawing Sheets

(56) References Cited

U.S. PATENT DOCUMENTS

| | | | |
|---|---|---|---|
| 6,626,861 B1 * | 9/2003 | Hart et al. | 604/96.01 |
| 6,638,294 B1 * | 10/2003 | Palmer | A61F 2/013 606/200 |
| 7,316,704 B2 | 1/2008 | Bagaoisan et al. | |
| 7,604,649 B2 * | 10/2009 | McGuckin, Jr. | A61F 2/013 606/200 |
| 7,662,166 B2 * | 2/2010 | Boyle | A61F 2/013 606/200 |
| 7,896,840 B2 * | 3/2011 | Spencer | A61M 25/1002 604/101.01 |
| 7,922,741 B2 * | 4/2011 | Gilson | A61F 2/013 606/200 |
| 7,935,075 B2 * | 5/2011 | Tockman | A61N 1/057 600/109 |
| 7,993,366 B2 * | 8/2011 | Yassinzadeh | A61B 17/0057 606/191 |
| 8,034,022 B2 * | 10/2011 | Boatman | A61M 25/1011 604/101.01 |
| 8,083,761 B2 * | 12/2011 | Meens | A61F 2/958 606/192 |
| 8,221,317 B2 * | 7/2012 | Maynard et al. | 600/208 |
| 8,257,418 B2 * | 9/2012 | Meens | A61F 2/958 264/632 |
| 8,307,830 B2 * | 11/2012 | Clayton | 128/207.15 |
| 8,814,826 B2 * | 8/2014 | Foreman et al. | 604/96.01 |
| 2002/0042627 A1 * | 4/2002 | Brady | A61F 2/013 606/200 |
| 2002/0107541 A1 * | 8/2002 | Vale | A61F 2/013 606/200 |
| 2004/0015224 A1 * | 1/2004 | Armstrong et al. | 623/1.12 |
| 2004/0176798 A1 * | 9/2004 | Epstein et al. | 606/213 |
| 2007/0060863 A1 * | 3/2007 | Goeken | A61B 17/32072 604/22 |
| 2008/0078403 A1 * | 4/2008 | Clayton | 128/207.15 |
| 2008/0114367 A1 * | 5/2008 | Meyer | A61B 17/025 606/90 |
| 2008/0249461 A1 * | 10/2008 | Foreman et al. | 604/28 |
| 2009/0018569 A1 * | 1/2009 | Desai et al. | 606/191 |
| 2009/0054924 A1 * | 2/2009 | Brady | A61F 2/013 606/200 |
| 2009/0192453 A1 * | 7/2009 | Wesselmann | 604/101.01 |

* cited by examiner

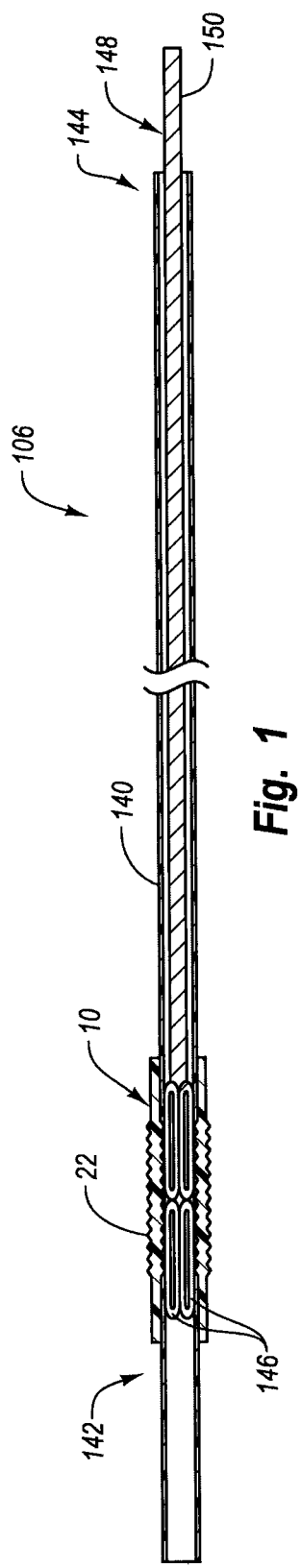
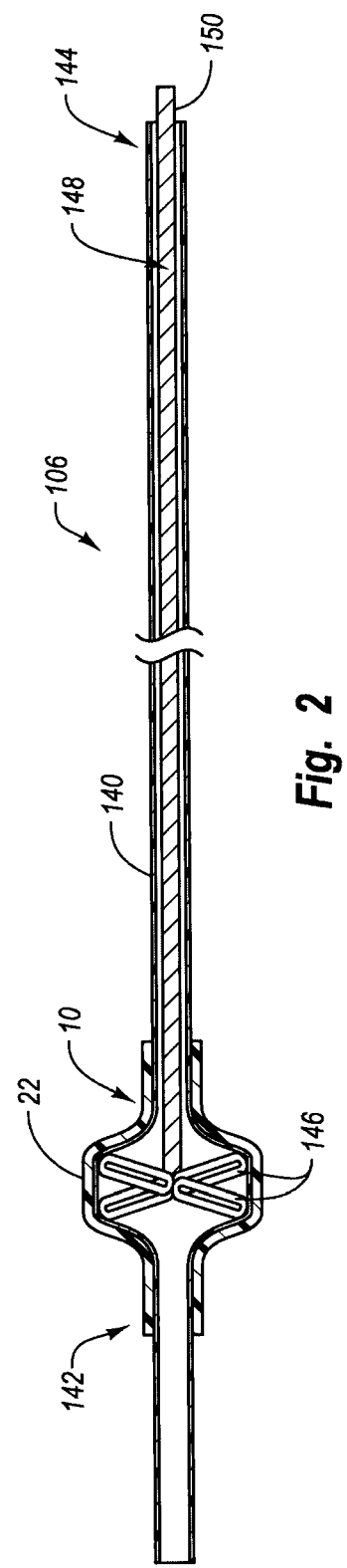

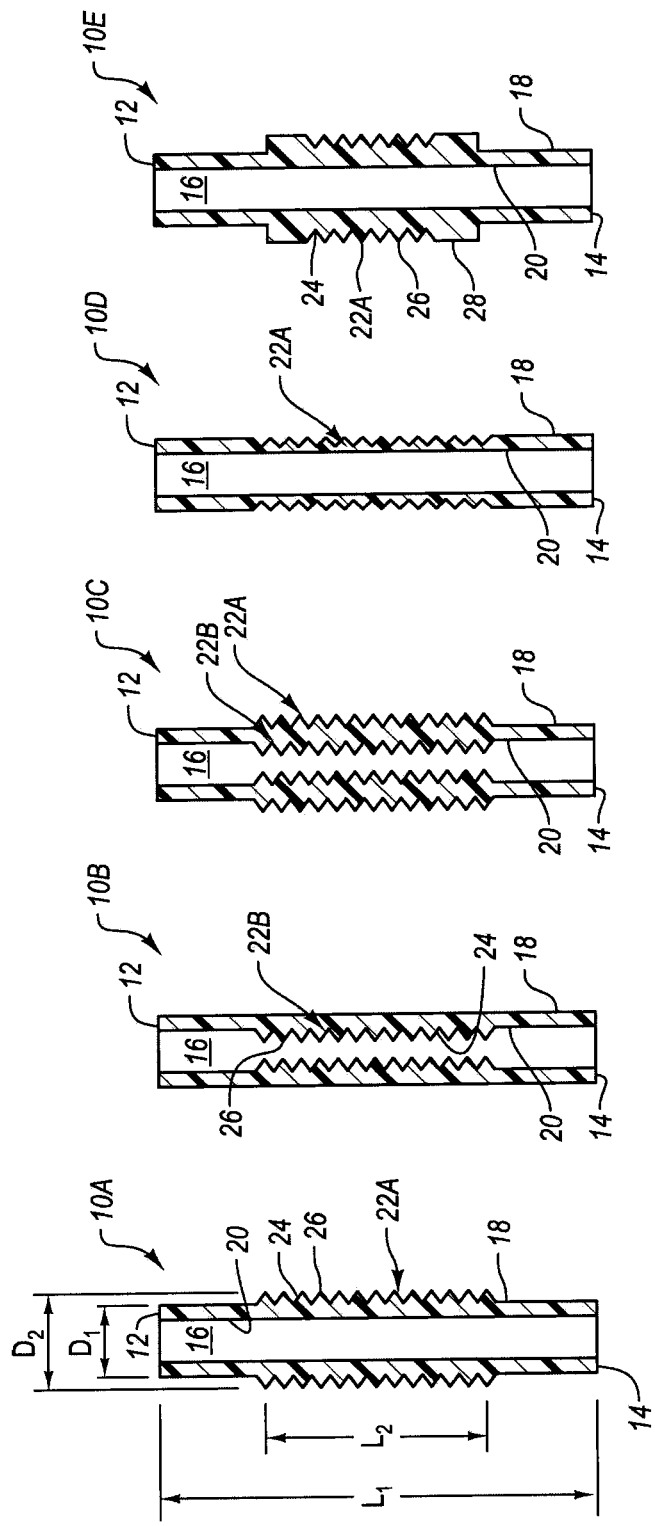

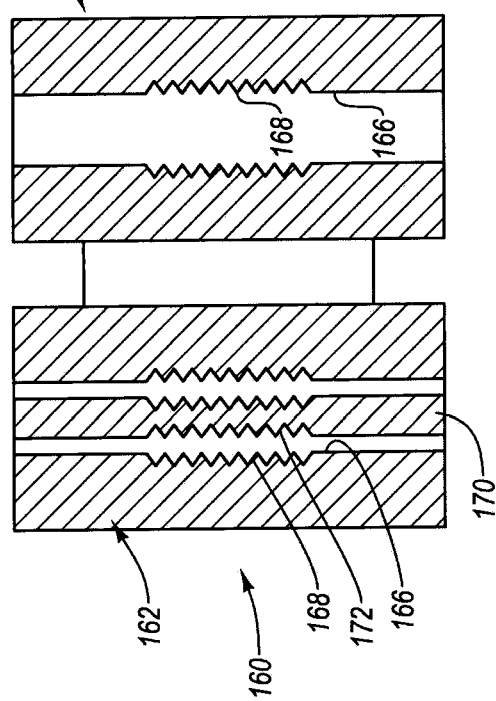
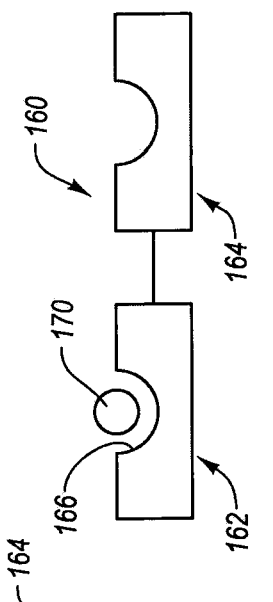

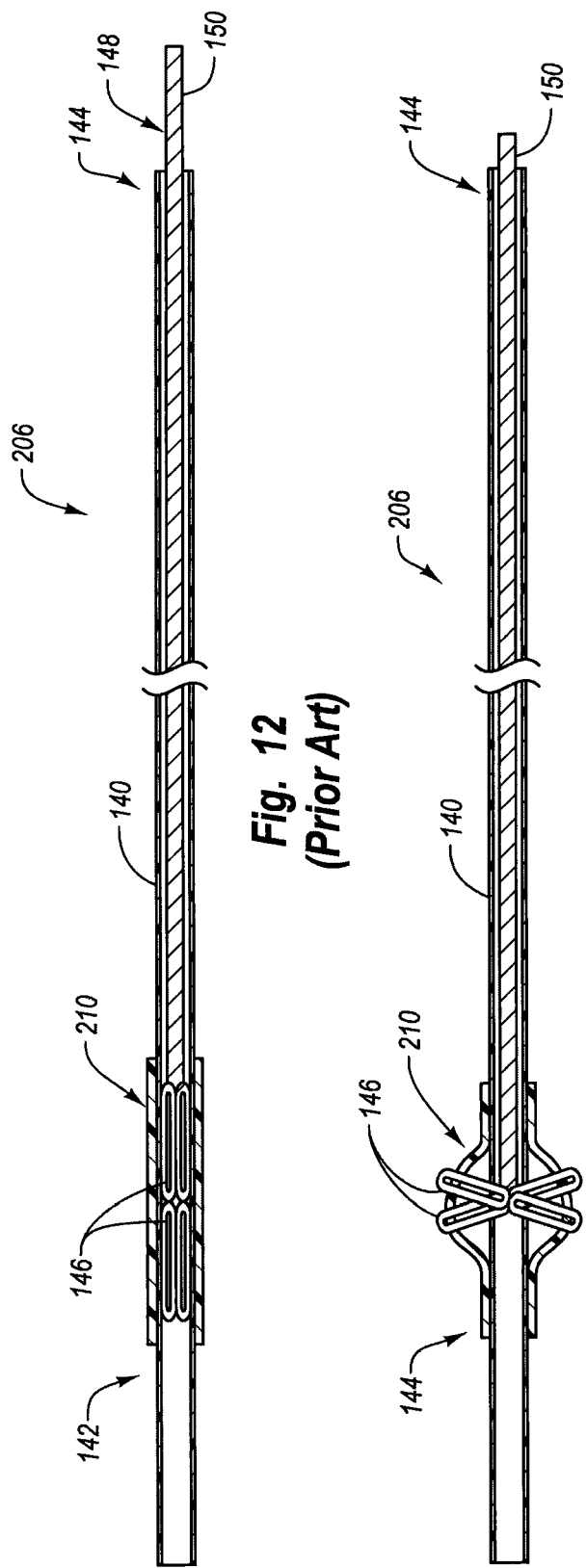

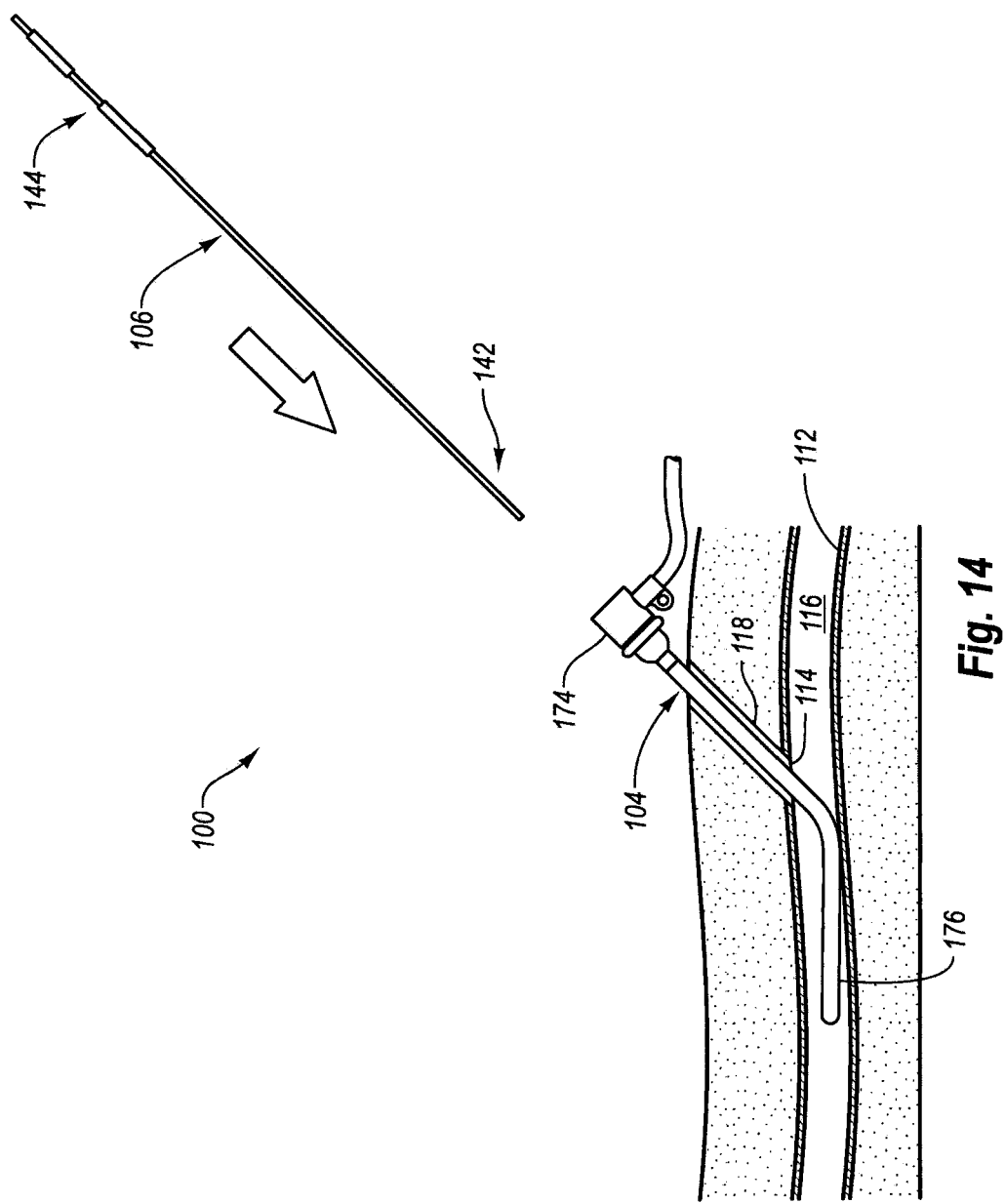

POLYMER MEMBRANE LOCATOR WITH BUILT-IN STRESS RELIEF STRUCTURE

CROSS-REFERENCE TO RELATED APPLICATION

This application claims the benefit of U.S. Provisional Patent Application No. 61/236,450 filed Aug. 24, 2009, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing pad at the tissue puncture site. Successful deployment of the sealing pad includes ejection from within the closure device sheath to a location in alignment with and adjacent to the tissue puncture along an outer surface of the vessel. Misalignment of the sealing pad relative to the tissue puncture may result in improper sealing of the tissue puncture. Failure to contact the sealing pad against the outer surface of the vessel may also result in an improper seal.

In extra vascular devices there is no intravascular component used to create a compressive sealing force between the inner wall of the artery and the exterior device. Without an opposite applied force from within the vessel, it may be difficult to place the sealing pad in alignment with the tissue puncture and obtain a proper seal. Some extra vascular devices use staples and resorbable components to seal a tissue puncture but do not utilize a compressive force to press the sealing pad against the tissue puncture since there is no opposing structure inside of the artery against which to apply the compressive force. Staples may be used to stab into the tissue adjacent to the tissue puncture to hold the sealing pad in place. Other types of devices use resorbable components such as collagen plugs that use the radial force of the collagen as it swells to hold the sealing pad in place adjacent to the tissue puncture. Such devices have proven to be less effective in placing a sealing pad adjacent to a tissue puncture and maintaining the sealing pad to provide a proper seal.

SUMMARY

One aspect of the present disclosure relates to a tissue puncture locator device that includes an expandable member, a deformable membrane, and an actuator. The expandable member is movable between an unexpanded position and an expanded position. The deformable membrane extends around at least a portion of the expandable member. The membrane has a stress relief portion. The actuator is operable to move the expandable member between the unexpanded and expanded positions.

The stress relief portion may include a plurality of circumferential grooves. The stress relief portion may include an increased thickness portion positioned at a location between proximal and distal ends of the membrane. The stress relief portion may include a plurality of circumferential protrusions. The stress relief portion may be arranged along at least an internal surface of the membrane. The stress relief portion may be arranged along at least an external surface of the membrane. The stress relief portion may provide increased flexibility along a portion of the membrane. The stress relief portion may extend along less than an entire length of the membrane.

The expandable member may be arranged generally longitudinally in the unexpanded position, and at least a portion of the expandable member may extend in a lateral direction when in the expanded position. The expandable member may include at least two elongate members coupled together at a pivot point, wherein the elongate members are arranged generally longitudinally in the unexpanded position and arranged generally laterally in the expanded position. The tissue puncture may be a vessel puncture in a vessel, and the expandable member moves between unexpanded and expanded positions within the vessel.

Another aspect of the present disclosure relates to a vascular closure device that includes a temporary anchor member and an expandable membrane. The membrane covers at least a portion of the anchor member and includes at least one of a groove and a protrusion that is configured to limit stress in the expandable member when expanded by the anchor member.

The vascular closure device may further include an actuator configured to move the anchor member between expanded and retracted positions. The vascular closure device may further include a sealing member configured for positioning adjacent to a vessel puncture at a proximal location, wherein the anchor member is configured for temporary positioning adjacent to the vessel puncture at a distal location. The vascular closure device may further include a carrier member, the anchor member and membrane may be positioned at a distal portion of the carrier member, and the actuator may be accessible at a proximal portion of the carrier member. The anchor member may include at least two elongate members and comprise a metal material.

A further aspect of the present disclosure relates to a method of locating a tissue puncture. The method may include providing a puncture locating device comprising an expandable member and a membrane, wherein the membrane is arranged covering at least a portion of the expandable member and includes at least one stress relief structure positioned adjacent to the expandable member. The method may also include inserting the expandable member through the tissue puncture, and moving the expandable member from an unexpanded position to an expanded position, wherein in the expanded position the stress relief structure is expanded by the expandable member and the expandable member is arranged to resist retraction through the tissue puncture.

The stress relief structure may include at least one of a circumferentially arranged groove and a circumferentially arranged protrusion, and moving the expandable member from the unexpanded position to the expanded position at least partially flattens the groove or protrusion. The method may further include advancing a sealing member toward the tissue puncture while the expandable member is in the expanded position, and withdrawing the expandable member through the sealing member while the expandable member is in the unexpanded position. The membrane may define an inner surface and an outer surface, and the stress relief structure is defined along at least one of the inner and outer surfaces.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the present disclosure.

FIG. 1 is a side view of an example arteriotomy locator wire assembly in an unexpanded state in accordance with the present disclosure.

FIG. 2 is a side view of the arteriotomy locator wire assembly shown in FIG. 1 in an expanded state.

FIGS. 5-9 are cross-sectional side view of several example locator membranes for use in the wire assemblies of FIGS. 1-4.

FIG. 10 is a side view of an example mold assembly for use in making a locator membrane in accordance with the present disclosure.

FIG. 11 is an end view of the mold assembly of FIG. 10.

FIG. 12 is a side view of an arteriotomy locator wire assembly in an unexpanded state according to the prior art.

FIG. 13 is a side view of the arteriotomy locator wire assembly shown in FIG. 1 in an expanded state.

FIG. 14 is a side view of an example tissue puncture treatment assembly in accordance with the present disclosure, wherein the introducer is inserted into a vessel and the locator wire of FIG. 1 is positioned for insertion into the introducer.

Throughout the drawings, identical reference numbers designate similar, but not necessarily identical, elements.

DETAILED DESCRIPTION

Figure 3:
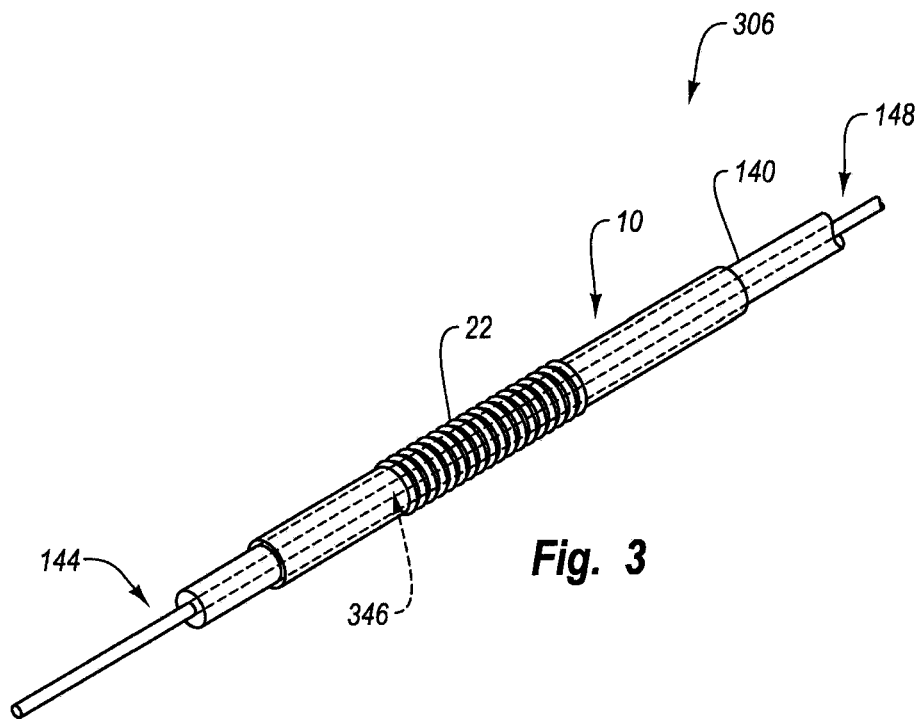
FIG. 3 is a side view of another example arteriotomy locator wire assembly in an unexpanded state in accordance with the present disclosure.

As mentioned above, vascular procedures are conducted throughout the world and require access to an vessel through a puncture. In some cases, the vessel is a femoral artery. To close the puncture following completion of the procedure, many times a closure device is used to position a sealing pad within a percutaneous incision adjacent to the puncture. Orientation of the sealing pad relative to the puncture may be particularly useful for successful sealing of the puncture.

An anchor positioned within the vessel may provide a sealing or partial sealing function for the puncture prior to disposing the sealing pad adjacent to the puncture. The anchor may be constructed and positioned within the vessel to at least partially block or occlude a flow of blood through the puncture.

An anchor positioned within the vessel may also act as a locator or reference member during placement of the sealing pad relative to the puncture. The anchor is positioned adjacent the puncture on an internal wall of the vessel. The sealing pad is then deposited adjacent to the puncture on an outer wall of the vessel. Proper positioning of the sealing pad relative to the puncture may be particularly difficult without an anchor provided internal the vessel that provides a locator or reference point function.

In some puncture sealing procedures, compressing the sealing pad against the puncture may improve sealing of the puncture. In order to apply a compressing force to the sealing pad, it may be helpful to provide an anchor positioned within the vessel on an opposite side of the vascular wall from the sealing pad. The anchor may be held against the interior surface of the vessel wall as the sealing member is compressed in the distal direction against an exterior surface of the vessel wall to create a seal against the outer surface of the vessel in the area adjacent to the puncture.

Some types of anchors for use with closure devices include a mechanical expansion feature. This type of anchor sometimes includes a membrane that covers at least portions of the expansion feature. The membrane may be expandable or at least deformable within the vessel upon opening or expanding of the mechanical expansion feature within the membrane. The mechanical expansion feature may include a plurality of metal spokes, rods, pedals, or link members that are actuatable from an unexpanded position for passage through the puncture, to a radially outward expanded position within the membrane while positioned within the vessel to retain the anchor within the vessel. When the expansion member is in the expanded position within the vessel, the expansion member and membrane together function as an anchor within the vessel for the closure device. The expansion member and membrane may also function as a locator that indicates to the operator a position of the tissue puncture.

Membranes used to cover at least portions of an anchor that include mechanical expansion features as discussed above may be susceptible to damage or failure due to expansion of the expandable member. Referring to FIGS. 12 and 13, a membrane 210 of a locator wire assembly 206 is shown having failed to expose portions of an anchor member 146 when the anchor member 146 is in an expanded position (see FIG. 13). The mechanical expansion features of the anchor may include pointed, sharp features that tend to create stress concentration points in the membrane. When the anchor moves from the unexpanded position to the expanded position, the membrane may be stretch and expanded. In some arrangements, portions of the membrane may reduce in thickness as the anchor moves into the expanded position, while other portions of the membrane may increase in thickness, fold, bend, crease, or be deformed in some fashion.

The example closure devices described with reference to the attached figures include a temporary anchor member that is operable between an unexpanded, generally longitudinally arranged position and an expanded, generally laterally arranged position. The term "temporary" as used herein related to the anchor member is defined as an anchor that provides an anchoring or locating function for a limited time. The temporary anchor member is maintaining in the vessel for a limited time and then manually removed from the vessel. A temporary anchor may be different from other types of anchor members that are deposited and left in the vessel. In some cases, these alternative types of anchor members comprise a bioresorbable material that is absorbed into the body over time.

In one arrangement, the temporary anchor member is covered at least in part by a membrane. The membrane includes features that provide reduced stress in the membrane to limit the possibility of the membrane failing. In some arrangements, the membrane may include a stress relief portion or stress relief structure. The stress relief portion may include at least one recess or groove, at least one protrusion, at least one increased thickness portion, or at least one decreased thickness portion. In some arrangements, the stress relief portion may include a different material composition than other portions of the membrane. The stress relief portion may include material that has, for example, a higher flexibility property or an increased strength property. In at least some examples, the membrane includes an elastic material that returns to its original shape after the anchor moves from the expanded back to the unexpanded position.

While the vascular instruments shown and described below include procedure sheaths and puncture closure devices, the application of principles described herein are not limited to the specific devices shown. The principles described herein may be used with any medical device. Therefore, while the description below is are directed primarily to vascular procedures and certain embodiments of a vascular closure device. However, the general principles related to vascular puncture locators may be applicable to other devices and procedures outside of vascular closure devices and the placement of sealing pads.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

FIGS. 1-2 illustrate an example arteriotomy locator wire assembly 106 for the use with a tissue puncture treatment assembly (i.e., tissue puncture treatment assembly 100 described in further detail below). The locator wire assembly 106 includes a locator tube 140, a distal end portion 142, a proximal end portion 144, at least one expandable anchor member 146, a membrane 10, and an actuator member 148.

The locator wire assembly 106 is constructed for insertion through a tissue puncture to temporarily position the expandable anchor member 146 and associated membrane 10 on an opposite side of the tissue puncture. The anchor member 146 is activated from an unexpanded state (see FIG. 1) to an expanded state (see FIG. 2) by application of force to the actuator member 148 that moves the actuator member 148 relative to the locator tube 140. In one example, the actuator member 148 is advanced or retracted along the longitudinal axis of the locator wire assembly 106 relative to the locator tube 140 to move the anchor member from the unexpanded to expanded positions.

The anchor member 146 shown in FIGS. 1 and 2 includes a plurality of paddle members. The paddle members are aligned generally with a longitudinal axis of the locator wire assembly 106 when in the unexpanded position. The paddle members move to a generally radially outward or transverse orientation when in the expanded position. The paddle members of the anchor member 146 may be characterized as being generally elongate features and may be referenced as elongate expandable members. The paddle members may be connected together with, for example, hinge connections that provide relative pivotal motion between at least some of the paddle members of the anchor member 146. Various expandable anchor member constructions are disclosed in, for example, U.S. Pat. No. 6,056,769 and U.S. Pat. No. 7,316,704, which are hereby incorporated in their entireties by this reference.

Figure 4:
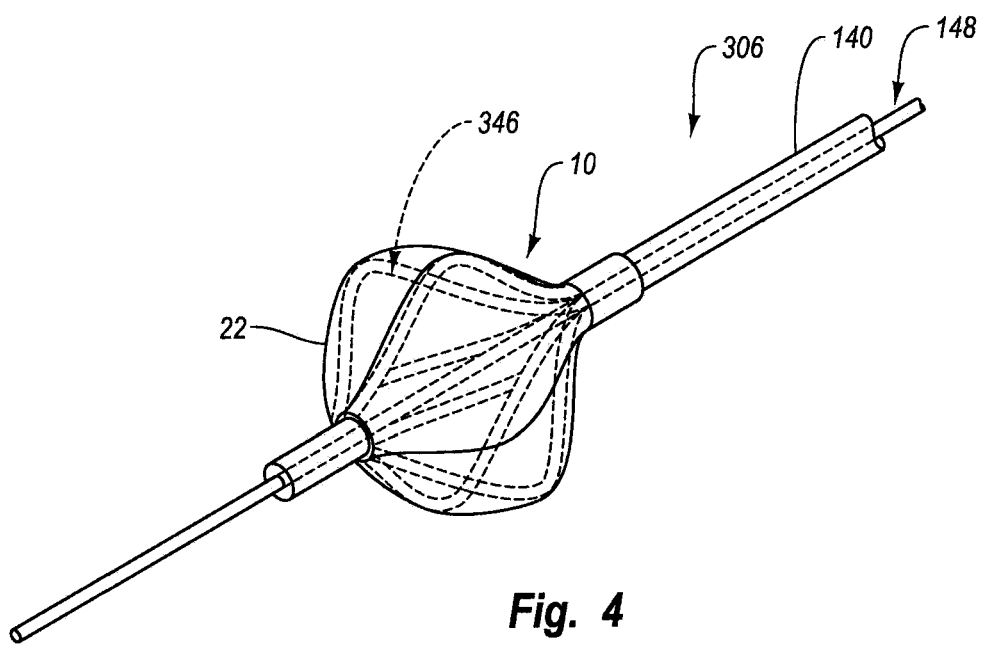
FIG. 4 is a side view of the arteriotomy locator wire assembly shown in FIG. 3 in an expanded state.

Another example anchor member 346 is shown and described with reference with FIGS. 3-4. The anchor member 346 is a part of a locator wire assembly 306 and includes a locator tube 140, distal and proximal end portions 142, 144, a membrane 10, and an actuator member 148. The anchor member 146 includes a plurality of elongate lengths of anchor material that are arranged side-by-side and connected at opposing proximal and distal ends (see FIG. 3). When the anchor member 346 is activated by operation of the actuator member 148, the spaced apart lengths of anchor material separate in the radial or transverse direction as shown in FIG. 4. Expanding the anchor member 146 may expand and stretch the membrane 10. The membrane 10 may be deformed into different shapes having different material thickness upon expansion of the anchor member 146.

The membrane 10 shown in FIGS. 1-4 includes first and second end portions 12, 14, a lumen 16, an outer surface 18, an inner surface 20, and a stress relief portion or structure 22 (see FIG. 5). The stress relief portion 22 may include a plurality of grooves 24, protrusions 26, or a combination of grooves and protrusions. The stress relief portion 22 may be defined along an outer surface 18 such as the stress relief portion 22A shown in FIG. 5. Other arrangements are possible for the stress relief portion. For example, the stress relief portion may be defined along at least a portion of an inner surface 20 as shown in FIG. 6 as stress relief portion 22B. FIG. 7 illustrates stress relief portions 22A, 22B defined along at least portions of the outer and inner surfaces 18, 20.

A stress relief portion may be constructed primarily as a plurality of protrusions that increase a thickness of the membrane 10 along at least a portion of the length of the membrane. FIGS. 5-7 include stress relief portions 22A, 22B that are constructed primarily as increased thickness portions. FIG. 8 illustrates a stress relief portion 22A that has a decrease in thickness defined as a plurality of grooves along at least a portion of a length of a membrane 10D. FIG. 9 illustrates another example membrane 10E that includes an increased thickness portion 28 along at least a portion of the length of the membrane 10E. A plurality of grooves 24 may be defined in the increased thickness portion 28 to create a stress relief portion 22A. The grooves 24 may result in a plurality of peaks or protrusions 26 also defined in increased thickness portion 28. As clearly shown in FIG. 3, the grooves 24 may be circular or form circles that extend around an entire circumference of the stress relief portion 22A. Similar increased thickness portion construction may be defined along the interior surface 20 as well as the outer surface 18 (e.g., see FIG. 9).

The example membranes 10A-E and other membrane structures disclosed herein may have a total length $L_1$ and diameter or maximum width dimension $D_1$, The stress relief portion 22 may have a total length $L_2$ and a maximum width or diameter dimension $D_2$. The length $L_2$ is typically less than the length $L_1$, although it may be possible to provide the length $L_2$ equal to $L_1$ in some arrangements. The dimension $D_2$ is typically within about 50% either greater or smaller than the dimension $D_1$, and more preferably in the range of about 10% to about 30% greater or smaller than the dimension $D_1$. The dimension $D_2$ is typically not much greater than the dimension $D_1$ in order to maintain a minimum outer profile for the membrane 10 to provide ease of inserting the membrane 10 with anchor member 146 (when unexpanded) through a tissue puncture of a patient.

The stress relief portion 22 may extend around a portion of the outer and inner surfaces 18, 20 of the membrane 10. In other arrangements, the stress relief portion 22 extends around an entire circumference either on the outer or inner surface 18, 20, or both of the outer and inner surfaces 18, 20. In some arrangements, a single structures such as a groove 24 or a protrusion 26 may define the stress relief portion 22. The grooves, protrusions and other structure that define the stress relief portion 22 may have any cross-sectional shape and size (e.g., square or triangular cross-sectional shape). In some arrangements, the stress relief portion includes a plurality of spaced apart features around an inner or outer circumference of the membrane such as divots or hemispherical protrusions. In further arrangements, the structures defining the stress relief portion 22 may have a generally helical arrangement along the outer or inner surfaces 18, 20. In still other arrangements, the structure defining the stress relief portion 22 may be arranged generally longitudinally in parallel with the longitudinal axis of the membrane 10.

The stress relief portion 22 of the membrane 10 is typically constructed to limit or reduce the incidence of failure (i.e., rupture, tearing, puncture, or wear) due to movement of the anchor member 146 from the unexpanded to expanded positions. The stress relief portion 22 may be constructed to distribute or dissipate stress points in the membrane 10 at the interface between the anchor member 146 and the membrane 10. In some constructions, the stress relief portion includes an increased thickness to provide additional strength and thereby resistance to failure. In other arrangements, the stress relief portion includes structure or material that tend to spread the stress imposed by point contact forces applied to the membrane 10 by the anchor member 146. In some arrangements, the stress relief portion provides increased flexibility or elasticity properties that limit stress in the material of the membrane and thereby reduced the possibility of failure.

In one example, (i.e., see FIG. 5 and the comparison of FIGS. 1 and 2) at least some aspects of the stress relief portion (i.e., the grooves 24 or protrusions 26) may elastically deform thereby substantially flattening the structure of the stress relief portion 22.

In one example, the locator wire assembly 106 may be used to both locate a vessel puncture and to achieve and maintain temporary hemostasis. Typically, an introducer sheath is inserted into the vessel puncture and the locator wire assembly 106 is inserted through the introducer sheath into the vessel. Once the anchor member 146 is positioned inside the vessel and extending beyond a distal end of the introducer, the anchor member 146 may be expanded radially or laterally (i.e., into the expanded state show in FIGS. 2 and 4) such that the anchor member covered by the membrane 10 has a maximum dimension that is larger than the maximum size of the puncture and the inner diameter of the introducer. The locator wire is then retracted proximally until the expanded anchor member engages the distal end of the introducer. The introducer and locator wire are together retracted proximally until the expanded anchor member is engaged against an inner surface of the vessel.

Engaging the expanded anchor member against the inner surface of the vessel adjacent to the vessel puncture may provide hemostasis as well as provide an anchor function. Typically, the anchor member 146 together with the membrane 10 comprises sufficient tactile and structural rigidity so that the expandable anchor member 146 does not inadvertently retract through the vessel puncture and out of the vessel.

The actuator member 148 may be locked in an axially advanced or rotated position relative to the locator tube 140 to maintain the anchor member in the expanded position. The actuator member 148 may be manually released or actuated in some manner to permit the anchor member 146 to attain its original unexpanded shape. In some arrangements, the anchor member includes elastic material that facilitates the radially outward expansion of the anchor member to provide temporary hemostasis and anchoring for a tissue puncture treatment assembly, and then return of the anchor member to its original unexpanded orientation that permits retraction through the vascular puncture.

Typically, the membrane 10 comprises a polymeric material that has elastic properties. Many polymeric and non-polymeric elastic materials may be used, including, for example, polyurethane, silicone, polyvinyl chloride, and rubber-based materials. The membrane 10 may be formed using, for example, injection molding, casting, milling, cutting, and other methods of construction.

An example mold assembly 160 for forming the membrane 10 is shown in FIGS. 10 and 11. The mold assembly 160 may include first and second mold members 162, 164 that define a mold cavity 166. The first and second mold members 162, 164 may include cavity stress relief forming features 168 along a internal surface thereof that defines the mold cavity 166. A core 170 may be positioned in the mold cavity 166 to help define the lumen 16 of the membrane 10. The core 170 may include core stress relief forming features 172 along a length thereof. The cavity and core stress relief forming features 168, 172 may define at least in part the stress relief portion 22 of the membrane 10 along at least one of the inner and outer surfaces 18, 20.

Forming the membrane 10 using the mold assembly 160 may include at least some of the following method steps in any given order: connecting the first and second mold members 162, 164 together to define the mold cavity 166, positioning the core 170 in the mold cavity 166, filling the mold cavity 166 with a curable material, curing the curable material to form the membrane 10, disconnecting the first and second mold members 162, 164 to remove the membrane 10 from the mold cavity 166, and removing the core 170 from the membrane 10.

Other mold assembly constructions are possible that include more or fewer parts. For example, the mold assembly may include a single mold member that defines the mold cavity. In another example, the mold assembly includes a core member that includes a plurality of segments that are removable from opposite ends of the completed mold member. Multiple curable materials may be used to fill the mold cavity 166 to provide a membrane with a plurality of materials in its composition. The cavity and core stress relief forming features 168, 172 may have any construction to provide any desired stress relief portion features.

Referring now to FIGS. 14-20, an example tissue puncture treatment assembly 100 is described with reference to treatment of a vessel puncture 114. The tissue puncture treatment assembly 100 is merely exemplary of the many devices that may utilize the various membrane and anchor structures disclosed herein. The functionality, features, and methods of use described herein with reference to FIGS. 14-20 represent one application of the membrane and anchor structures in a tissue puncture treatment device.

The tissue puncture treatment assembly 100 includes a sealing pad delivery device 102, an introducer 104, and a locator wire assembly 106 (i.e., the locator wire assembly 106 described above with reference to FIGS. 1-2). The tissue puncture treatment assembly 100 may also include a tissue tract dilator (not shown) that is used to expand an internal size of a percutaneous incision 118 through which the locator wire assembly 106 is inserted. The tissue puncture treatment assembly 100 is used to seal closed a vessel puncture 114 that is defined in a vessel 112. The vessel 112 includes a vessel interior 116. The vessel puncture 114 is accessible from outside a patient via the percutaneous incision 118.

Referring first to FIG. 14, the introducer 104 is inserted through the percutaneous incision 118 and vessel puncture 114 until a distal end 176 of the introducer 104 is positioned within the vessel interior 116. A hub 174 of the introducer 104 defines an opening into the introducer through which the locator wire assembly 106 is advanced. The locator wire assembly 106 includes a distal end portion 142 and a proximal end portion 144. Typically, the distal end portion 142 is advanced through the hub 174 until the distal end portion 142 extends distally beyond the distal end 176 of the introducer.

The tissue tract dilator (not shown) may be advanced over the locator wire assembly 106 after the locator wire has been advanced into the vessel 112. The tissue tract dilator may be used to enlarge at least the percutaneous incision 118 to a size great enough for insertion of a sealing pad into the percutaneous incision 118.

Figure 15:
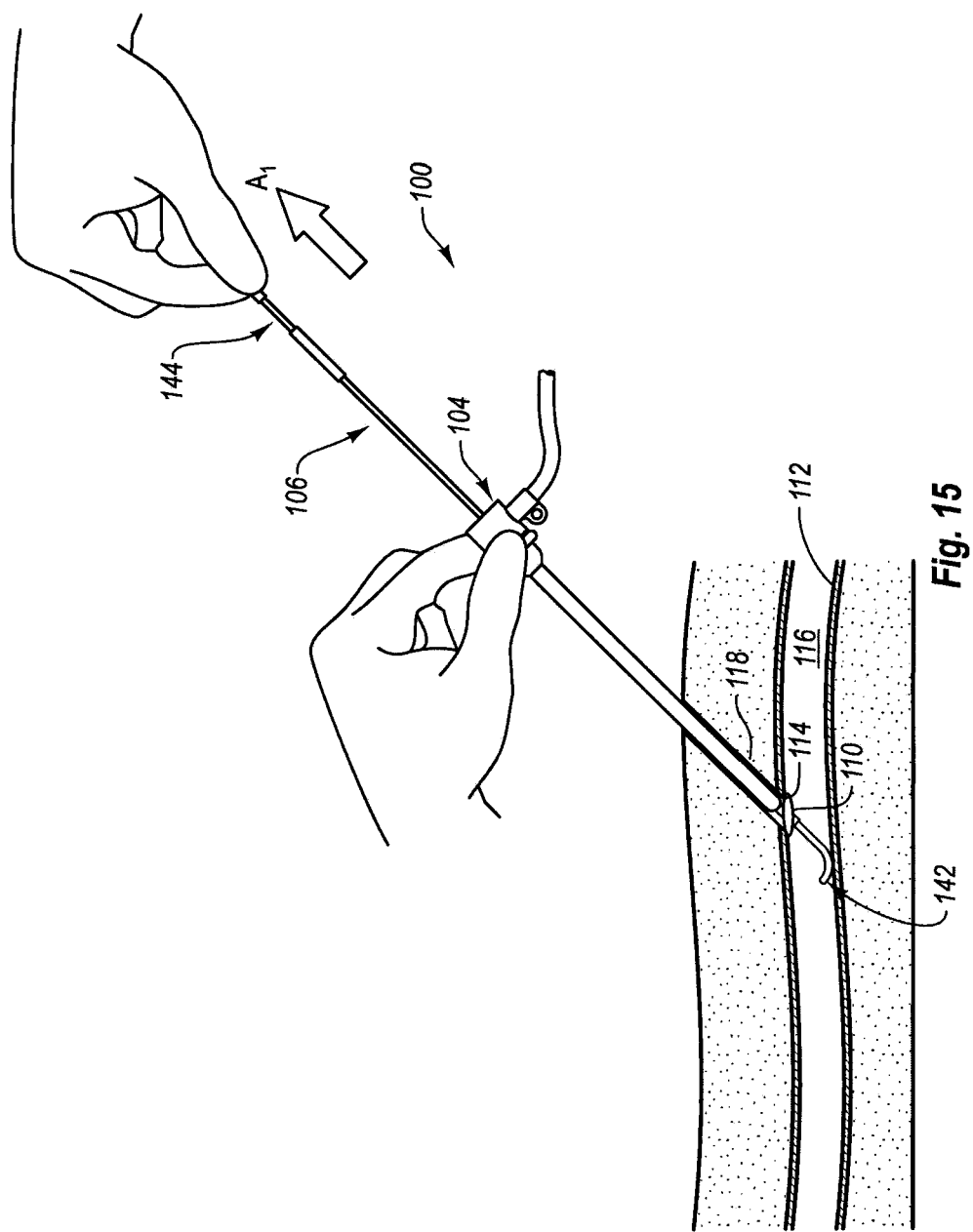
FIG. 15 is a side view of the tissue puncture treatment assembly of FIG. 14 with the introducer and locator wire being retracted to engage the expanded membrane against an interior wall of the vessel.

Referring now to FIG. 15, the locator wire assembly 106 is advanced distally through the introducer 104 until the distal end portion 142 is positioned within the vessel interior 116 at a location distal of the distal end 176 of the introducer. The locator wire assembly 106 is actuated to move the anchor member 146 into a radially outward expanded state. In one example, the locator wire assembly 106 includes an actuator member 148 that extends through a locator tube 140. A grasping portion 150 of the actuator member 148 is moved relative to the locator tube 140 to actuate the expandable anchor members 146 between the unexpanded position shown in FIG. 14 and the expanded position shown in FIG. 15.

The anchor member 146 has a maximum diameter or width dimension when in the expanded state shown in FIG. 15. Typically, the maximum expanded dimension is greater than a maximum width dimension of the vessel puncture 114. The maximum expanded dimension is also typically greater than an internal dimension of the introducer 104 at the distal end 176. The operator may apply a force to locator wire assembly 106 in the proximal direction $A_1$ shown in FIG. 15 to contact the anchor member 146 against a distal end surface of the introducer 104.

The operator may concurrently retract the introducer 104 and locator wire assembly 106 in the direction $A_1$ until the anchor member 146 contacts against an inner surface of the vessel 112 adjacent to the vessel puncture 114. Typically, the anchor member 146 provides at least some hemostasis at the vessel puncture 114. The operator may feel a slight resistance to retraction in the direction $A_1$ once the expandable anchor member 146 contacts against the inner surface of the vessel 112.

Figure 16:
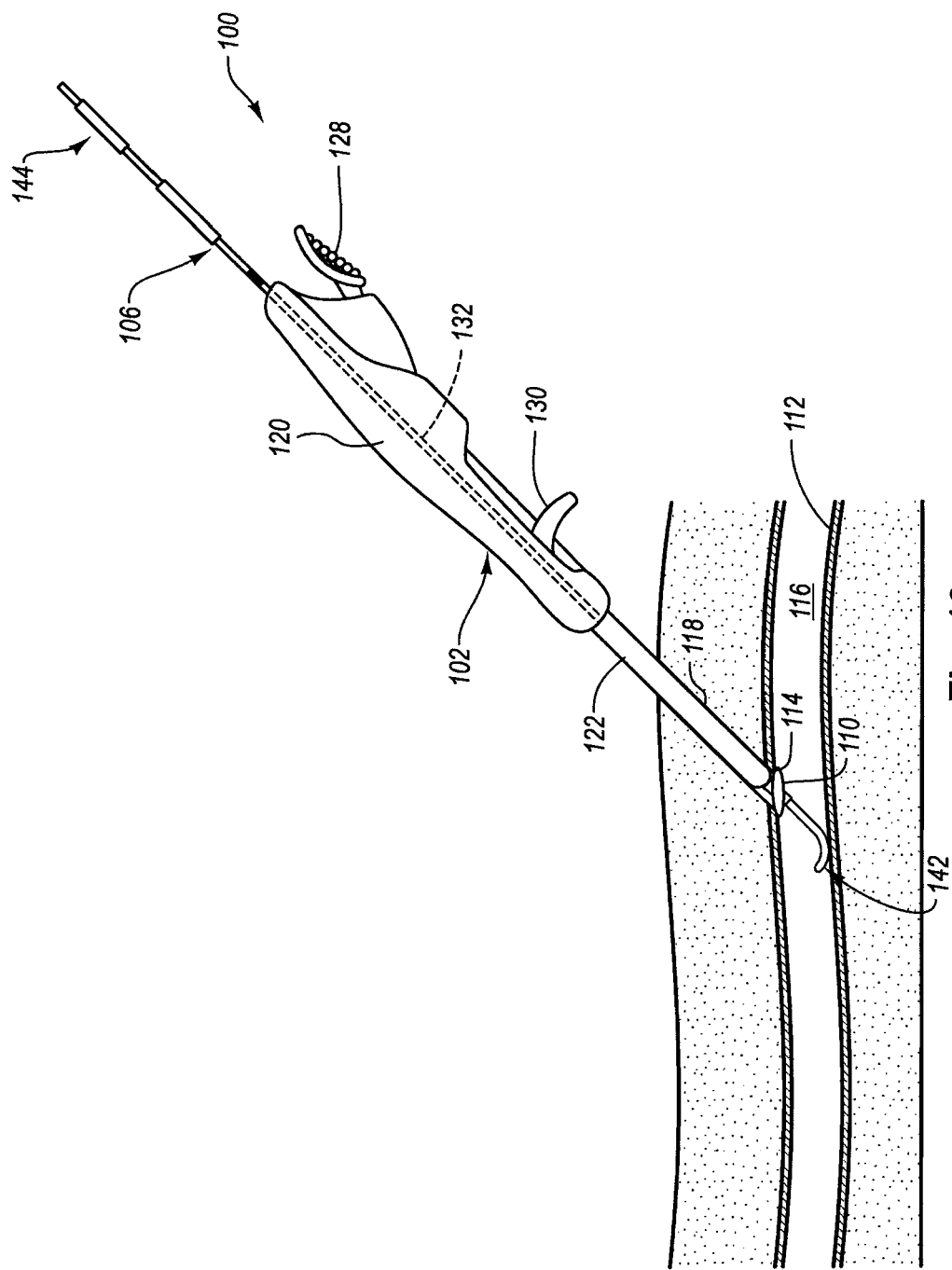
FIG. 16 is a side view of the tissue puncture treatment assembly of FIG. 15 with a sealing pad delivery device advanced over the locator wire and into the percutaneous incision.

Referring to FIGS. 15 and 16, the operator maintains at least some tension on the locator wire assembly 106 in the direction $A_1$ to maintain hemostasis while removing the introducer 104 in direction $A_1$ from off the locator wire assembly 106. The sealing pad delivery device 102 is advanced distally over the locator wire assembly 106 and into the percutaneous incision 118. The dilator (not shown) may be advanced over the locator wire assembly 106 and into the percutaneous incision 118 to dilate the percutaneous incision 118 in an intermediate step between removing the introducer 104 and advancing the sealing pad delivery device 102.

The sealing pad delivery device 102 includes a housing 120, a carrier tube 122 extending from a distal end of the housing 120, a positioning tube 124 positioned within the carrier tube 122, and a sealing pad 126 positioned within the carrier tube 122 and located distal of the positioning tube 124. The sealing pad delivery device 102 may also include a wire locking member 128, a tube retracting actuator 130, and a wire aperture 132. The wire aperture 132 extends from a proximal end of the housing 120 to a distal end of the carrier tube 122 and is sized to receive the locator wire assembly 106.

Figure 17:
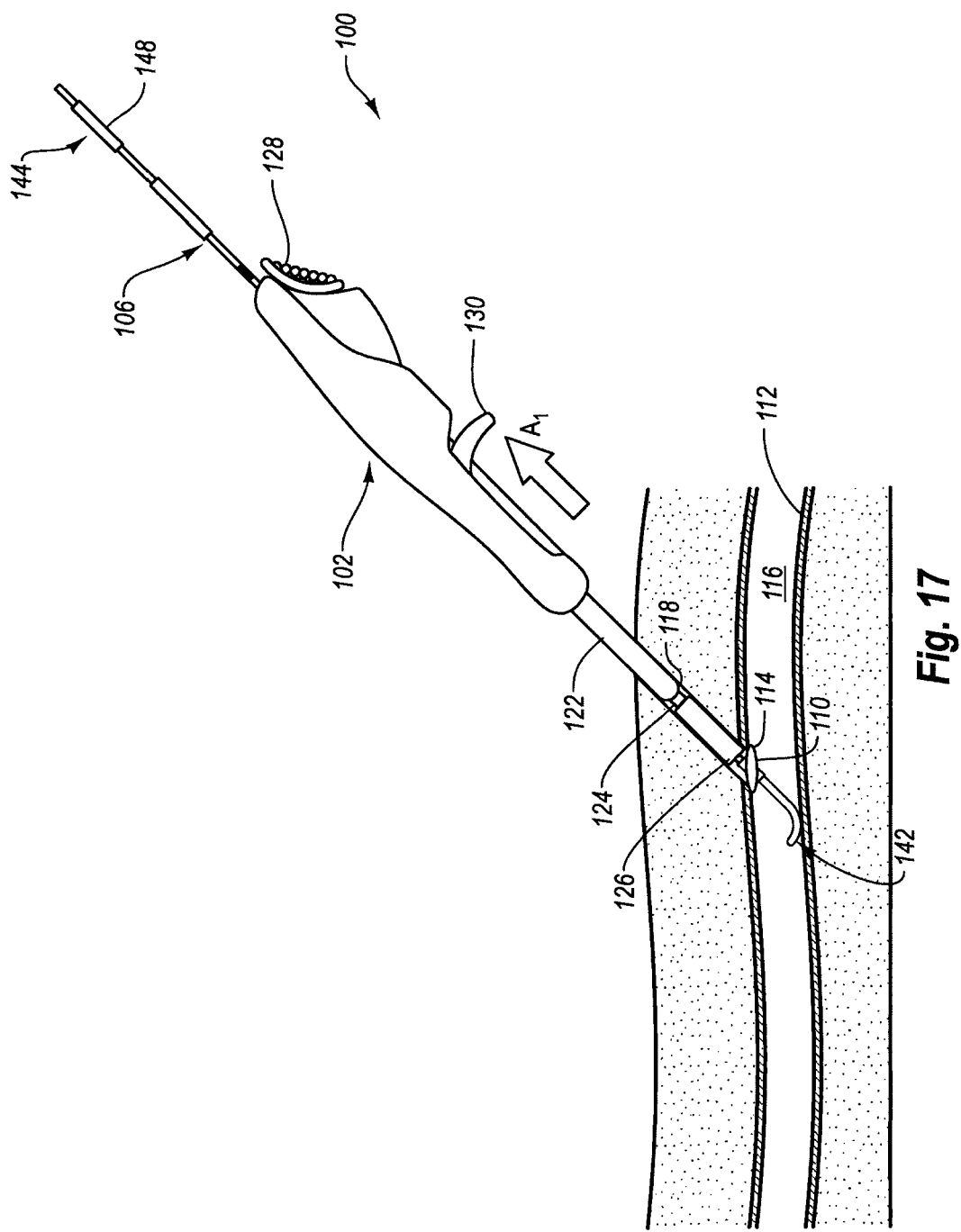
FIG. 17 is a side view of the tissue puncture treatment assembly of FIG. 16 with the sealing pad delivery device actuated to expose a sealing pad within the percutaneous incision.

Referring now to FIG. 17, once the sealing pad delivery device 102 is positioned within the percutaneous incision 118 with tension being applied to the locator wire assembly 106, the wire locking member 128 is actuated to fix an axially position of the sealing pad delivery device 102 relative to the locator wire assembly 106. In at least one example, the wire locking member 128 contacts the locator wire assembly 106 directly with a force sufficient to limit movement of the sealing pad delivery device 102 in the axial direction relative to the locator wire assembly 106 when applying forces that are typical in treating a vessel puncture 114. Many alternative constructions are possible for the wire locking member 128 to provide the desired resistance to relative movement between the sealing pad delivery device 102 and the locator wire assembly 106.

A force is applied to the tube retracting actuator 130 in the proximal direction $A_1$ to retract the carrier tube 122 at least partially into the housing 120. Typically, the carrier tube 122 is retracted with the tube retracting actuator 130 a distance sufficient to fully expose the sealing pad 126 within the percutaneous incision 118. In at least some arrangements, exposing the sealing pad 126 within the percutaneous incision 118 also advances the sealing pad 126 in the distal direction. In one example, the positioning tube 124 may be used to distally advance the sealing pad 126. In other arrangements, the positioning tube 124 holds the sealing pad in a fixed position during retraction of the carrier tube 122.

The anchor member 146, held in contact with the inner surface of the vessel 112 adjacent to the vessel puncture 114, may provide an anchor to resist axial forces applied to the sealing pad 126 in the distal direction. The anchor function of anchor member 146 limits movement of the sealing pad 126 through the vessel puncture 114 and may facilitate some compression of the sealing pad 126 toward the vessel puncture 114.

Figure 18:
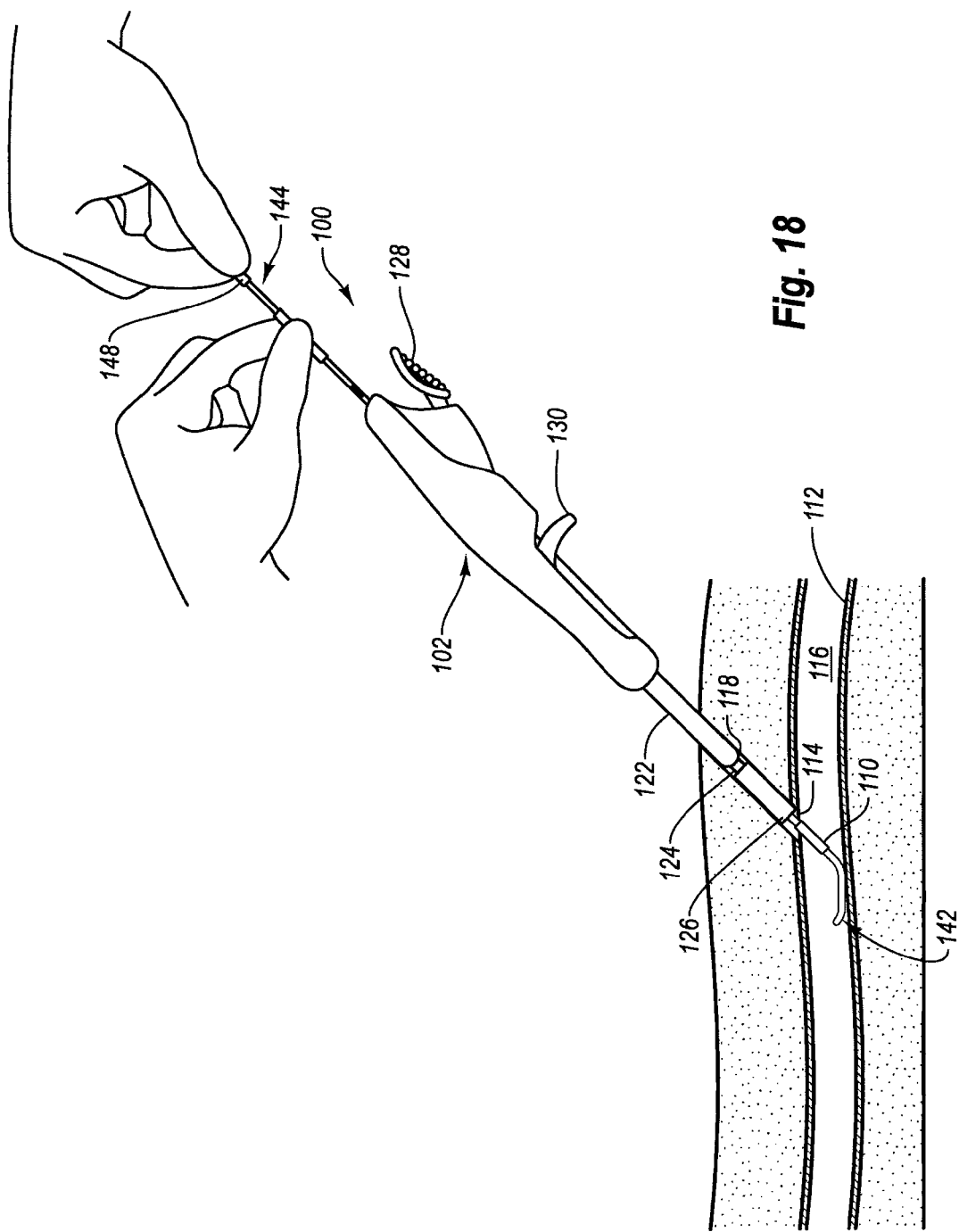
FIG. 18 is a side view of the tissue puncture treatment assembly FIG. 17 with the locator wire being actuated to move the membrane into an unexpanded state.

Referring now to FIG. 18, the wire locking member 128 is released so that the sealing pad delivery device 102 may be moved relative to the locator wire assembly 106. The locator wire assembly 106 is then advanced in the distal direction until the anchor member 146 is moved out of contact with the inner wall of the vessel 112. The anchor member 146 is moved into the uncompressed, unexpanded state.

Figure 19:
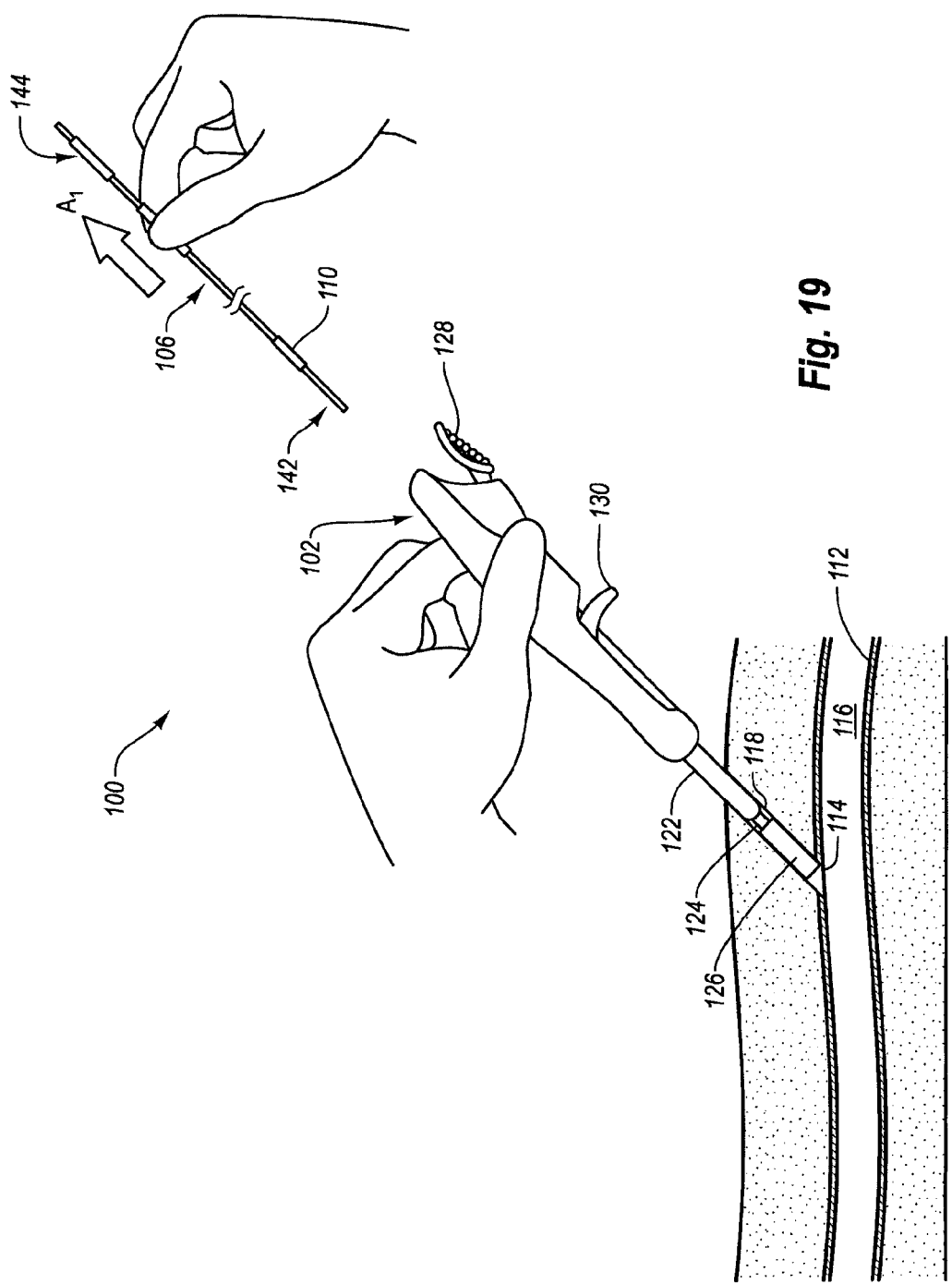
FIG. 19 is a side view of the tissue puncture treatment assembly of FIG. 18 with the locator wire being retracted through the sealing pad and removed from the sealing pad delivery device.
Figure 20:
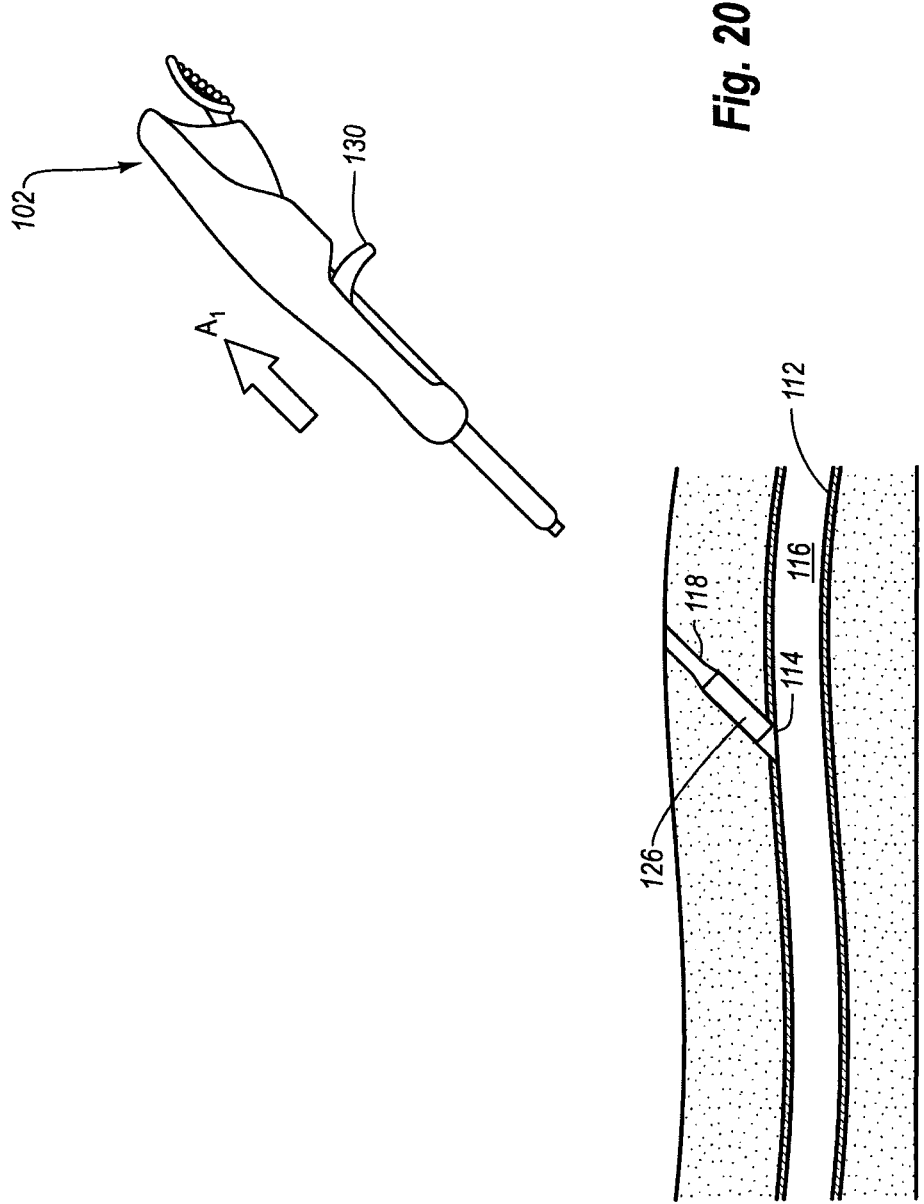
FIG. 20 is a side view of the tissue puncture treatment assembly of FIG. 19 with the sealing pad delivery device removed from the percutaneous incision.

Referring now to FIG. 19, the locator wire assembly 106 is advanced proximally out of the vessel 112, through the sealing pad 126, and out of the sealing pad delivery device 102 while holding the sealing pad delivery device 102 in a fixed position relative to the vessel 112. Referring to FIG. 20, the sealing pad delivery device 102 is retracted proximally while leaving behind the sealing pad 126 within the percutaneous incision 118. Typically the sealing pad 126 comprises an expandable material that expands to fill the percutaneous incision 118 at least at a location adjacent to the vessel puncture 114. In at least one example, the sealing pad 126 comprises a collagen material. The sealing pad 126 is typically configured to provide hemostasis in the vessel puncture 114 and percutaneous incision 118.

Many other constructions are possible for the various features of the tissue puncture treatment assembly 100 described above with reference to the attached figures. In particular, aspects of the locator wire assembly 106 including various arrangements for the membranes 10, 110 and other example membranes and membrane features described above may be changed or modified in accordance with the teachings provided herein.

Furthermore, alternative methods and treatment techniques using the membrane and anchor structures disclosed herein may be possible. In one alternative method, locating the vessel puncture using the anchor structure and membrane in the expanded state may occur concurrently with deploying the sealing pad within the percutaneous incision. In one example, the tissue puncture sealing device is assembled with the sealing pad arranged at a fixed distance from the anchor member and simultaneously exposed in the percutaneous incision adjacent to the tissue puncture while locating the vessel puncture with the expanded anchor member.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture locator device, comprising:
an expandable member movable between an unexpanded position and an expanded position, the expandable member comprising a plurality of expandable wires;
a deformable membrane extending around at least a portion of the expandable member, the membrane having a stress relief portion, the stress relief portion comprising an outer surface, an inner surface, and a total length, the outer surface including a plurality of grooves, each groove of the plurality of grooves having a closed-curve circular configuration, having a unique longitudinal position along the stress relief portion, and extending around an entire circumference of the stress relief portion at the unique longitudinal position, the plurality of grooves configured to reduce stress in the membrane during radial expansion of the membrane, the plurality of grooves being positioned on the membrane along the total length of the stress relief portion, the membrane being elastically deformable to at least partially flatten the stress relief portion upon radial expansion of the membrane, the inner surface having an internal diameter, the internal diameter being constant across the stress relief portion;
an actuator operable to move the expandable member between the unexpanded and expanded positions.

2. The tissue puncture locator device of claim 1, wherein the stress relief portion includes an increased thickness portion positioned at a location between proximal and distal ends of the membrane.

3. The tissue puncture locator device of claim 1, wherein the stress relief portion includes a plurality of circumferential protrusions.

4. The tissue puncture locator device of claim 1, wherein the stress relief portion is arranged along at least an internal surface of the membrane.

5. The tissue puncture locator device of claim 1, wherein the stress relief portion is arranged along at least an external surface of the membrane.

6. The tissue puncture locator device of claim 1, wherein the stress relief portion provides increased flexibility along a portion of the membrane.

7. The tissue puncture locator device of claim 1, wherein the expandable member is arranged generally longitudinally in the unexpanded position, and at least a portion of the expandable member extends in a lateral direction when in the expanded position.

8. The tissue puncture locator device of claim 1, wherein the expandable member includes at least two elongate members coupled together at a pivot point, wherein the elongate members are arranged generally longitudinally in the unexpanded position and arranged generally laterally in the expanded position.

9. The tissue puncture locator device of claim 1, wherein the tissue puncture is a vessel puncture in a vessel, and the expandable member moves between unexpanded and expanded positions within the vessel.

10. The tissue puncture locator device of claim 1, wherein the plurality of circularly configured grooves decrease thickness of the deformable membrane along the outer surface relative to an outer surface of the deformable membrane adjacent to the stress relief portion.

11. A tissue puncture locator device, comprising:
an expandable member movable between an unexpanded position and an expanded position, the expandable member comprising a plurality of expandable wires;
a deformable membrane extending around at least a portion of the expandable member, the membrane comprising a first end portion, a second end portion, and a stress relief portion extending circumferentially around the membrane between the first end portion and the second end portion, the stress relief portion having an outer surface, an inner surface, and a total length, the outer surface having at least one of a plurality of grooves and a plurality of protrusions, the outer surface having a decreased circumference relative to the first end portion and the second end portion at the plurality of grooves or plurality of protrusions, the plurality of grooves or plurality of protrusions being circular in configuration, each of the grooves or protrusions of the plurality of grooves or the plurality of protrusions having a unique longitudinal position along the stress relief portion and extending around an entire circumference of the stress relief portion at the unique longitudinal position, the plurality of grooves or the plurality of protrusions being positioned on the membrane along the total length of the stress relief portion, the stress relief portion providing stress relief in the membrane during radial expansion of the membrane, the membrane being elastically deformable to at least partially flatten the stress relief portion upon radial expansion of the membrane, the inner surface having an internal diameter, the internal diameter being constant between ends of the stress relief portion;
an actuator operable to move the expandable member between the unexpanded and expanded positions.

12. The tissue puncture locator device of claim 11, wherein the tissue puncture closure device is configured to extend through a vessel puncture and temporarily seal the vessel puncture internally without stopping flow through the vessel.

13. The tissue puncture locator device of claim 11, wherein the stress relief portion is arranged along at least an external surface of the membrane.

14. The tissue puncture locator device of claim 11, wherein the stress relief portion provides increased flexibility along a portion of the membrane.

15. The tissue puncture locator device of claim 11, wherein the expandable member is arranged generally longitudinally in the unexpanded position, and at least a portion of the expandable member extends in a lateral direction when in the expanded position.

16. The tissue puncture locator device of claim 11, wherein the stress relief portion is elastically deformable.

17. The tissue puncture locator device of claim 11, wherein stress relief portion includes a decreased thickness portion along at least a portion of a length of the membrane.

18. A tissue puncture locator device, comprising:
an expandable member movable between an unexpanded position and an expanded position, the expandable member comprising a plurality of expandable wires;
a deformable membrane extending around at least a portion of the expandable member, the membrane comprising a first end portion, a second end portion, and a stress relief portion positioned between the first end portion and the second end portion, the stress relief portion having an outer surface, an inner surface, and a total length, the outer surface having a plurality of circularly configured grooves forming closed curves around the stress relief portion, each closed curve forming a circular path along which a starting point is also an ending point, each groove of the plurality of circularly configured grooves having a unique longitudinal position along the total length of the stress relief portion and extending around an entire circumference of the stress relief portion at the unique longitudinal position, the plurality of circularly configured grooves being positioned along the total length of the stress relief portion of the membrane to provide stress relief in the membrane during radial expansion of the membrane, the outer surface having a decreased circumference at the plurality of circularly configured grooves relative to the first end portion and the second end portion, the membrane being elastically deformable to at least partially flatten the stress relief portion upon radial expansion of the membrane, the inner surface forming a constant-diameter cylinder within the outer surface;
an actuator operable to move the expandable member between the unexpanded and expanded positions.

19. The tissue puncture locator device of claim 18, wherein the plurality of circularly configured grooves have a decreased thickness relative to a portion of the membrane that is not part of the stress relief portion.

* * * * *